United States Patent
Thacker

(10) Patent No.: US 9,662,370 B2
(45) Date of Patent: *May 30, 2017

(54) PEPTIDYL DIACYLGLYCERIDES

(75) Inventor: James Douglas Thacker, Doylestown, PA (US)

(73) Assignee: Therimunex Pharmaceuticals, Inc., Doylestown, PA (US)

(*) Notice: Subject to any disclaimer, the term of this patent is extended or adjusted under 35 U.S.C. 154(b) by 244 days.

This patent is subject to a terminal disclaimer.

(21) Appl. No.: 12/989,059

(22) PCT Filed: Apr. 24, 2009

(86) PCT No.: PCT/US2009/041595
§ 371 (c)(1),
(2), (4) Date: Jan. 26, 2011

(87) PCT Pub. No.: WO2009/132231
PCT Pub. Date: Oct. 29, 2009

(65) Prior Publication Data
US 2011/0123611 A1 May 26, 2011

Related U.S. Application Data

(60) Provisional application No. 61/047,464, filed on Apr. 24, 2008.

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| A61K 38/10 | (2006.01) | |

(52) U.S. Cl.
CPC .................... *A61K 38/10* (2013.01)

(58) Field of Classification Search
CPC .................. A61K 38/10; B21D 5/12
See application file for complete search history.

(56) References Cited

U.S. PATENT DOCUMENTS

| | | | |
|---|---|---|---|
| 5,256,641 A | | 10/1993 | Yatvin et al. |
| 5,554,728 A | * | 9/1996 | Basava ............ C07F 9/10 530/327 |
| 5,688,771 A | * | 11/1997 | Penney et al. ........... 514/3.7 |
| 6,716,963 B1 | | 4/2004 | Henkin et al. |
| 6,812,339 B1 | | 11/2004 | Venter et al. |
| 7,608,589 B2 | * | 10/2009 | Thacker .................. 514/1.1 |
| 2003/0109437 A1 | | 6/2003 | Averback et al. |
| 2011/0123611 A1 | | 5/2011 | Thacker |
| 2012/0238491 A1 | * | 9/2012 | Thacker .................. 514/2.4 |

FOREIGN PATENT DOCUMENTS

| | | |
|---|---|---|
| CN | 1714101 A | 12/2005 |
| WO | 92/14490 | 9/1992 |
| WO | 2007/014193 A2 | 2/2007 |
| WO | 2009/132231 A2 | 10/2009 |

OTHER PUBLICATIONS

Illum. Nanoparticulate SYstems for Nasal Delivery of Drugs: A Real Improvement over Simple Systems?. J of Pharmaceutical Sciences, Mar. 2007. vol. 96, No. 3, pp. 473-483.*
Hamm et al., Caprine serum fraction immunomodulator as supplemental treatment of lower respiratory disease in the horse, Equine vet J. (2002) 34 (1) 71-75.
Illum, Nanoparticulate Systems for Nasal Delivery of Drugs: A Real Improvement over Simple Systems?, Journal of Pharmaceutical Sciences, vol. 96, No. 3, Mar. 2007.
Thacker et al., 1-Peptidyl-2-arachidonoyl-3-stearoyl-sn-glyceride: An Immunologically Active Lipopeptide from Goat Serum (*Capra hircus*) is an Endogenous Damage-Associated Molecular Pattern, J. Nat. Prod., Jun. 15, 2009.
Thacker et al., NLRP3 Inflammasome is a Target for Development of Broad-Spectrum Anti-Infective Drugs, Antimicrobial Agents and Chemotherapy, 2012, p. 1921-1930.

* cited by examiner

*Primary Examiner* — Marcela M Cordero Garcia
(74) *Attorney, Agent, or Firm* — Jon M. Gibbs; Lowndes, Drosdick, Doster, Kantor & Reed

(57) ABSTRACT

Peptide and peptides that may be covalently linked to a lipid and methods of using such peptides and lipopeptides to prevent or treat disease are disclosed herein.

31 Claims, 10 Drawing Sheets

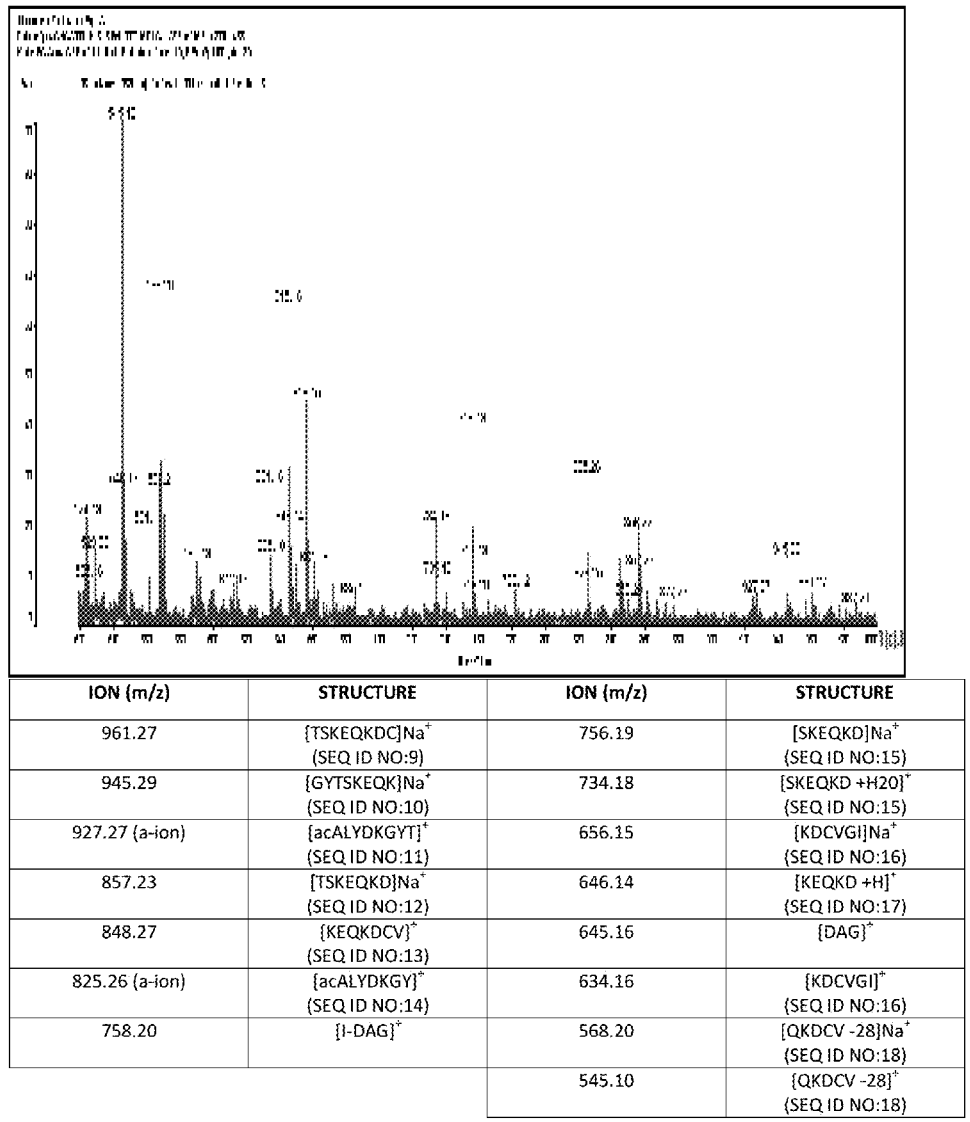

| ION (m/z) | STRUCTURE | ION (m/z) | STRUCTURE |
|---|---|---|---|
| 961.27 | {TSKEQKDC}Na$^+$ (SEQ ID NO:9) | 756.19 | [SKEQKD]Na$^+$ (SEQ ID NO:15) |
| 945.29 | {GYTSKEQK}Na$^+$ (SEQ ID NO:10) | 734.18 | [SKEQKD +H2O]$^+$ (SEQ ID NO:15) |
| 927.27 (a-ion) | {acALYDKGYT}$^+$ (SEQ ID NO:11) | 656.15 | {KDCVGI}Na$^+$ (SEQ ID NO:16) |
| 857.23 | {TSKEQKD}Na$^+$ (SEQ ID NO:12) | 646.14 | [KEQKD +H]$^+$ (SEQ ID NO:17) |
| 848.27 | {KEQKDCV}$^+$ (SEQ ID NO:13) | 645.16 | {DAG}$^+$ |
| 825.26 (a-ion) | {acALYDKGY}$^+$ (SEQ ID NO:14) | 634.16 | {KDCVGI}$^+$ (SEQ ID NO:16) |
| 758.20 | {I-DAG}$^+$ | 568.20 | [QKDCV -28]Na$^+$ (SEQ ID NO:18) |
|  |  | 545.10 | {QKDCV -28}$^+$ (SEQ ID NO:18) |

FIG. 4

PEPTIDYL DIACYLGLYCERIDES

CROSS-REFERENCE

In certain embodiments, the immuno-reactive peptide is of amino acid sequence XLYDKGYTSKEQKDCVGIX (SEQ ID NO:1) or XLYDKGYTPKEQKDCVGIX (SEQ ID NO:2) or inversions or mimetics thereof, wherein X is absent or a naturally occurring amino acid or mimetic thereof, a derivatized amino acid or a non-amino acid prosthetic group.

BACKGROUND

The biological role of the diacylglycerols has been well described in the literature. For instance it is well known that diacylglycerols participate in the transport of lipids as triglycerides and in association with soluble proteins such as the apolipoproteins, are transporters of cholesterol. Diacylglycerols are also known to have an intracellular signaling function. Intracellular, membrane bound phosphatidyl inositol-4,5-biphosphate is cleaved by the actions of the enzyme phospholipase C to release two intracellular messenger molecules, inositol triphosphate and membrane bound diacylglycerol (specifically 1-stearoyl-2-arachidonoyl glycerol). Diacylglycerol activates protein kinase C which activates transcription factor NFκB to up regulate the gene expression of various cytokines and chemokines. Peptidyl-2,3-diacylglyceride, or PDAG, has been implicated in immune function. More specifically, PDAG has a role in stimulating an immune response. U.S. application Ser. No. 11/459,772 (U.S. publication no. 2007/0197436) and other publications used herein to illuminate the background of the invention or provide additional details regarding the biological mechanisms, are incorporated by reference.

BRIEF SUMMARY OF THE INVENTION

Embodiments of the invention described herein include compounds that may stimulate an immune response that include an immuno-reactive peptide of from about 5 to about 25 amino acids covalently linked to a lipid. In some embodiments, the lipid may be a glyceride of general formula (I):

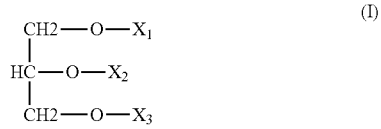

wherein $X_1$, $X_2$ and $X_3$ are selected from hydrogen, $C_2$ to $C_{25}$ fatty acid and a peptide, and at least one of $X_1$, $X_2$ and $X_3$ is a peptide. The fatty acid of embodiments may be saturated, unsaturated, or poly unsaturated fatty acids, and the peptide may be covalently linked to the lipid by an ester bond at the C-terminus of the peptide.

In certain embodiments, the immuno-reactive peptide is of amino acid sequence XLYDKGYTSKEQKDCVGIX or XLYDKGYTPKEQKDCVGIX or inversions or mimetics thereof, wherein X is absent or a naturally occurring amino acid or mimetic thereof, a derivatized amino acid or a non-amino acid prosthetic group.

Compounds of embodiments of the invention may further contain a pharmaceutically acceptable excipient and may be provided in a unit dose form that is consistent with an effective amount of the compound, and these embodiments may be considered pharmaceutical compositions.

Further embodiments of the invention, include methods which may include administering an effective amount of an agent made up of a peptide having about 5 to about 25 amino acids covalently linked to a lipid to a subject in need thereof, and stimulating an immune response. The peptide of embodiments of the invention may include a peptide or peptide fragment of amino acid sequence XLYDKGYTSKEQKDCVGIX (SEQ ID NO:1) or XLYDKGYTPKEQKDCVGIX (SEQ ID NO:2) or inversions or mimetics thereof, wherein X is absent or a naturally occurring amino acid or mimetic thereof, a derivatized amino acid or a non-amino acid prosthetic group.

Agents of embodiments of the invention may include a glyceride of general formula (I):

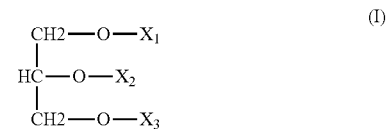

wherein $X_1$, $X_2$ and $X_3$ are selected from hydrogen, $C_2$ to $C_{25}$ fatty acid and a peptide, and at least one of $X_1$, $X_2$ and $X_3$ is a peptide. The fatty acid of embodiments may be saturated, unsaturated, or poly-unsaturated fatty acids. The peptide may be covalently linked to the lipid by an ester bond at the C-terminus of the peptide. The agent may be administered to stimulate an innate immune response, and tissue resident immune cells including, but not limited to, γδ cells, monocytes, NK cells, neutrophils, CD5+ B-cells and combinations thereof may be stimulated. In some embodiments, the tissue resident immune cells are stimulated when contacted by the peptide.

Agents of embodiments of the invention may include a glyceride of general formula (I) wherein the agent may be administered to stimulate an innate immune response, and non-immune cells including, but not limited to, epithelial cells, endothelial cells, fibroblasts, keratinocytes, hepatocytes and combinations thereof may be stimulated. In some embodiments, the tissue cells are stimulated when contacted by the peptide.

The immune response stimulated, in certain embodiments of the invention, may include stimulating an immune response for at least 1-3 days following administration of the agent, and in certain other embodiments, the immune response may be stimulated for a week or more.

In still other embodiments of the invention, the agent may be deposited in fatty tissue of the subject, and the agent may be administered by any method including enteral, parentaral, and topical delivery, mammary infusion, and combinations of these. Parenteral administration may include, but not limited to, intra-articular, intrasynovial, intrathecal, intraarterial, intravenous, intramuscular, subcutaneous and combinations thereof. Enteral administration may include, but not limited to, oral, peroral, rectal and combinations thereof, and topical administration may include, but not limited to, intranasal, intrarespiratory, epicutaneous, transdermal delivery and combinations thereof.

In some embodiments of the invention, the agent may be administered prior to exposure to a disease forming agent and may, in these embodiments, substantially prevent disease onset or progression. In other embodiments, the agent may be administered prior to disease. The agent may also be delivered following exposure to a disease forming agent and may, in these embodiments, may substantially arrest disease progression. In yet further embodiments, the agent may be delivered to the subject following disease onset to lessen the severity of the disease or reverse the course of the disease.

Further methods of embodiments of the invention include methods for treating an infection, methods for stimulating an immune response, methods for preventing disease, methods for preventing an infection, and combinations of these such as methods of treating a disease and preventing a secondary infection using agents and compositions of the invention described hereinabove.

Embodiments of the invention further include antibodies directed to compounds of the invention, and methods of treating inflammation such as, but not limited to, systemic inflammation, chronic inflammatory disease, and inflammation due to sepsis, non-septic injury, trauma, surgery or combinations thereof by administering the antibodies of embodiments of the invention. Antibodies of embodiments of the invention may be administered to a subject by any method known in the art including, but not limited to, enteral, parenteral, and topical delivery Antibodies of embodiments of the invention may also be linked to a selectable marker such as, but not limited to, a fluorescent marker such as a protein, or a quantum dot to make a probe, and methods of using such probes to detect and identify peptides in a sample, such as a biological, cell or tissue sample and cells or proteins that interact with such peptides.

DESCRIPTION OF DRAWINGS

For a fuller understanding of the nature and advantages of the present invention, reference should be made to the following detailed description taken in connection with the accompanying drawings, in which:

FIG. 4 shows the PSD MALDI-TOF mass spectrum of the PDAG hydrolysis products after mild acid hydrolysis. The table shows the major ion assignments to key peptide fragments accounting for the entire PDAG molecule in the present invention.

DETAILED DESCRIPTION

Figure 1A:
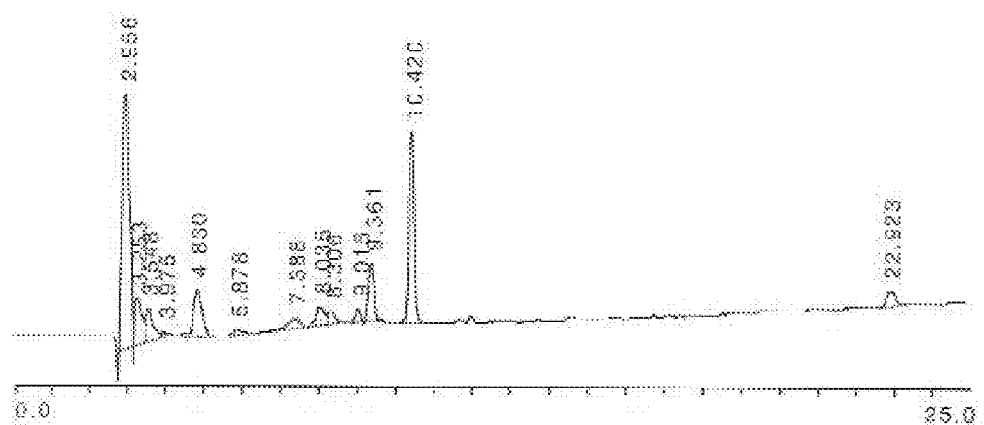
FIG. 1 shows a representative HPLC chromatogram of a serum fraction containing PDAG (FIG. 1A) and purified 1-peptidyl-2,3-diacylglyceride of the present invention (FIG. 1B).

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

An "adjuvant" refers to any substance which enhances the immune-stimulating properties of an antigen or the pharmacological effect of a drug.

As used herein, the term "about" means plus or minus 10% of the numerical value of the number with which it is being used. Therefore, about 50% means in the range of 45%-55

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the term "pharmaceutically acceptable salts, esters, amides, and prodrugs" refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

As used herein, the term "physiologically tolerable" and grammatical variations thereof, as they refer to compositions, carriers, diluents and reagents, are used interchangeably and represent that the materials are capable of administration upon a mammal without or with minimal production of undesirable physiological effects such as nausea, dizziness, rash, or gastric upset. In a preferred embodiment, the therapeutic composition is not antigenic when administered to a human patient or other animal for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted.

As used herein "subject" or "patient" refers to an animal or mammal including, but not limited to, human, dog, cat, horse, cow, pig, sheep, goat, chicken, monkey, rabbit, rat, mouse, etc.

"Disease" for purposes of the present invention may be any infectious agent such as, for example, viral particles, bacterial pathogens, and the like. "Diseased" as used in reference to a "diseased subject" may refer to any human or animal subject infected with an infectious agent. The "diseased subject" may or may not exhibit signs of infection such as, for example, known symptoms.

As used herein a "sample" includes a biological sample which can be tested by the methods of the present invention and include, but are not limited to, body fluids such as serum, plasma, whole blood, cerebrospinal fluid, lymph fluids, various external secretions (urine, respiratory, intestinal or genitourinary tract secretions, tears, etc.), etc.

As used herein, the term "therapeutic" means an agent utilized to treat, combat, ameliorate, prevent or improve an unwanted condition or disease of a patient. Embodiments of the present invention are directed to stimulate the innate immune response or modulation of the inflammatory response. The methods herein for use contemplate prophylactic use as well as curative use in therapy of an existing condition.

The terms "therapeutically effective" or "effective", as used herein, may be used interchangeably and refer to an amount of a therapeutic composition embodiments of the present invention—e.g. one or more of the peptidyl diacylglycerides or mimetics thereof. For example, a therapeutically effective amount of a composition comprising 1-peptidyl-2,3-diacylglyceride, or mimetics thereof, is a predetermined amount calculated to achieve the desired effect, i.e., to effectively stimulate an innate immune response in an animal to whom the composition is administered.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

One embodiment of the present invention may be directed to a 1-peptidyl-2,3-diacylglyceride or PDAG. Other embodiments of the invention may include compositions containing PDAGs, compositions that contain portions of PDAGs, compositions containing analogs of PDAG peptides and compositions containing peptide mimetics of PDAGs.

In embodiments of the invention, PDAGs, portions of PDAGs, analogs of PDAGs and mimetics of PDAGs may be provided to a subject and may stimulate therapeutic effects such as, but not limited to, inducing an immune response, and in certain embodiments, the immune response may be an innate immune response in the subject so provided. PDAGs, portions of PDAGs, analogs of PDAG and mimetics of PDAG, in other embodiments of the invention, may be administered to a subject undergoing treatment for disease, to a subject that is healthy, or to a subject that is healthy and may be exposed to disease, disease forming particles, or diseased humans and/or animals. In embodiments of the invention where PDAGs, portions of PDAGs, analogs of PDAGs and mimetics of PDAGs, and therapeutics containing PDAGs, portions of PDAGs, analogs of PDAGs and mimetics of PDAGs are provided to a subject that is healthy, the PDAGs, portions of PDAGs, analogs of PDAGs and mimetics of PDAG may promote the prophylactic activation of the immune system of the subject, and in certain embodiments prophylactic activation of innate immunity.

Without wishing to be bound by theory, the PDAGs, portions of PDAGs, analogs of PDAGs and mimetics of PDAGs, in embodiments of the invention, when provided to a subject may activate tissue resident immune cells in the subject. In some embodiments, the PDAGs, portions of PDAGs, analogs of PDAGs and mimetics of PDAGs may initiate an immune response, and in other embodiments, the immune response may be an innate immune response.

Embodiments of the present invention may also include methods of administering PDAGs, portions of PDAGs, analogs of PDAGs and mimetics of PDAG and therapeutics containing PDAGs, portions of PDAGs, analogs of PDAGs and mimetics of PDAGs such as, but not limited to, parenteral, enteral, or topical administration.

Other embodiments of the present invention include antibodies with specificity for the PDAGs, and methods for the use of such antibodies in depleting systemic or localized concentrations of PDAGs in a subject. In certain embodiments, the subject provided with antibodies specific to PDAGs may exhibit symptoms of immune disease such as, but not limited to, systemic inflammation, chronic inflammatory diseases, atherosclerotic disease, rheumatoid diseases, autoimmune diseases, and the like.

Still other embodiments of the invention include fluorescently labeled PDAGs, analogs of PDAGs, and fluorescently labeled antibodies or antibody fragments with specificity to PDAGs and methods for producing such fluorescently labeled PDAGs, analogs of PDAGs and antibodies. Fluorescently labeled PDAGs, analogs of PDAGs and antibodies may be used, in embodiments of the invention, as diagnostic tools to assess aspects of the immune system and immunopathology both in vitro and in vivo, and in some embodiments, subjects may include, but not limited to, subject exhibiting symptoms consistent with chronic inflammatory disease, autoimmune disease, atherosclerotic disease, diabetes and the like.

PDAGs described in various embodiments of the invention may include a peptidyl diacylglyceride having at least one peptide moiety covalently attached to a lipid moiety and are of the general formula I-peptidyl-2,3-diacylglyceride. In certain embodiments, the lipid moiety is 1-stearoyl-2-arachidonoyl glycerol.

The PDAGs described in embodiments of the invention may be of general formula (I):

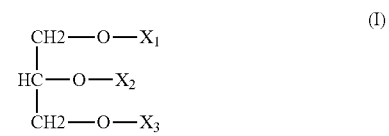

where $X_1$, $X_2$, and $X_3$ may be hydrogen, a peptide, peptide mimetic, or peptide analog, or a saturated, unsaturated, or polyunsaturated fatty acid having from about 1 to about 20 carbon atoms. In some embodiments of the invention, at least one of $X_1$, $X_2$, and $X_3$ may be a peptide, peptide mimetic, or peptide analog, and in others, more than one of $X_1$, $X_2$, and $X_3$ may be a peptide, peptide mimetic, peptide analog.

The peptide moiety of embodiments of the present invention may be made up of from between about 5 to about 25 amino acids and may include one or more naturally occurring, non-naturally occurring and chemically modified amino acids. These peptide moieties may weigh from about 1000 to about 3000 amu. Peptides encompassed by the present invention or mimetics thereof may include any amino acid sequence that confers the desired effect of activating immunity. Peptide moieties may be made and/or isolated prior to being attached to the lipid moiety and may be synthesized and isolated from a natural source such as, for example, human, animal, bacterium sources and the like or may be synthesized by any method known in the art. Peptides, peptide mimetics and peptide analogs so synthesized and isolated may be purified or concentrated by methods known to those of ordinary skill in the art such as, for example, by filtration, chromatography and the like. The peptide moiety may be covalently conjugated to the lipid moiety by esterification at the carboxy terminal carboxylic acid of the peptide, and in some embodiments, the peptide moiety may be conjugated to the lipid moiety through a phosphoester at the carboxy terminal carboxylic acid of the peptide.

The sequence of the peptide portion of the PDAG may vary among embodiments. For example, in one embodiment the peptide sequence may be XLYDKGYTSKEQKD-CVGIX (SEQ ID NO:1) or XLYDKGYTPKEQKDCVGIX (SEQ ID NO:2) or synthetic equivalents, peptide analogs or peptidomimetics thereof. In such embodiments, X may be absent or any naturally occurring amino acid or mimetic thereof, derivatized amino acids or non-amino acid prosthetic groups, and in particular embodiments, the N-terminal most amino acid may be N-acetyl alanine (acA). Without wishing to be bound by theory, the peptide sequences presented herein above may be representative of a larger class of peptides which may trigger an immune response in a mammal and, in particular, a human when administered alone or conjugated with a lipid moiety, for example, as a PDAG. Thus, any peptide isolated from virtually any source that performs such a function may be encompassed by embodiments of the invention including, for example, peptides associated with PDAGs isolated from sources such as, but not limited to, animals, mammals, humans, primates, cows, horses, pigs, birds, reptiles, insects, microorganisms, bacteria, and so on.

Peptides, peptide mimetics, or peptide analogs that are covalently conjugated to a lipid moiety to make up PDAGs may be considered and will hereinafter be referred to as "PDAG lipopeptides".

For example, PDAGs may be synthesized as follows. PDAG peptides or PDAG peptide mimetics may be made using solid-phase synthetic methods such as, for example, an FMOC synthesis protocol with extended HBTU/HOBt coupling cycles and pre-loaded Wang resins. Following synthesis, the peptide side chain protective groups may be cleaved and the peptide may be released from the resin with Reagent-K. The peptide may then be extracted from synthesis buffers using for example diethyl ether extraction and lyophilization. Reversed phase C-18 purification may be used to further purify the resultant crude peptides and may be followed by MALDI-TOF characterization to confirm the amino acid sequence.

The PDAG peptide or peptide mimetic may be covalently attached to the lipid portion of the PDAG using a two step process wherein, first, the PDAG peptide is synthesized as described above but without the de-protection step. The C-terminal carboxylic acid may then be activated with, for example, dicyclohexylcarbimide, and the peptide may be incubated in the presence diacylglycerol and a catalytic agent such as dimethylaminopyridine (DMAP). Esterification may occur during the incubation step allowing a peptidyl diacylglyceride to form. The peptide side chain protective groups may than be cleaved with Reagent K, and the peptidyl diacylglyceride product may be isolated and purified by chromatography. MALDI-TOF or ESI-MS" characterization may then be used to confirm the structure of the purified product.

The peptide portion of PDAGs of embodiments of the present invention may be modified such as, for example, by replacement of one or more of the naturally occurring side chains of the 20 genetically encoded amino acids (or D amino acids) with non-naturally occurring side chains, examples of non-naturally occurring side chains include, but are not limited to, alkyl, lower alkyl, 4-, 5-, 6-, to 7 membered alkaryl, amide, amide lower alkyl, amide di (lower alkyl), lower alkoxy, hydroxy, carboxy and the lower ester derivatives thereof, and with 4-, 5-, 6- to 7 membered heterocyclics to produce peptide mimetics. For example, proline analogs may be made in which the ring size of the proline residue is changed from 5 members to 4, 6, or 7 members. Cyclic groups may be saturated or unsaturated, and if unsaturated, may be aromatic or nonaromatic. Heterocyclic groups can contain one or more heteroatom such as for example nitrogen, oxygen, and/or sulphur and the like and may form groups including, but not limited to, the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups may be substituted or unsubstituted. Substituted heterocyclic groups may contain substituents such as but not limited to alkyl, alkoxy, halogen, oxygen, or substituted or unsubstituted phenyl. Peptidomimetics of PDAG peptides may also have amino acid residues that have been chemically modified for example by phosphorylation, sulfonation, biotinylation and the like.

A variety of techniques are available for constructing peptide mimetics with the same or similar desired biological activity as the corresponding native peptide but with better solubility, stability, and/or susceptibility to hydrolysis or proteolysis. Therefore, these characteristics of peptidomimetic compounds encourage their use in therapeutic applications since they may have increased cell permeability, greater affinity and/or avidity for cell receptors and prolonged biological half-life. Certain peptidomimetic compounds are based upon the amino acid sequence of the peptides of the invention. Often, peptidomimetic compounds are synthetic compounds having a three-dimensional structure (i.e., a "peptide motif") based upon the three-dimensional structure of a selected peptide. The peptide motif provides the peptidomimetic compounds with the desired biological activity, i.e., enhancing or stimulating an immune response, wherein the binding activity of the mimetic compound is not substantially reduced, and is often the same as or greater than the activity of the native peptide on which the mimetic is modeled.

Peptidomimetic design strategies are readily available in the art. One class of peptidomimetics contains a backbone that is partially or completely a non-peptide, but mimics the peptide backbone atom-for atom and comprises side groups that likewise mimic the functionality of the side groups of the native amino acid residues. Several types of chemical bonds, such as ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics is a small non-peptide molecule that binds to another peptide or protein, but which is not necessarily a structural mimetic of the native peptide. Yet another class of peptidomimetics has arisen from combinatorial chemistry and the generation of massive chemical libraries. These generally are novel templates which, though structurally unrelated to the native peptide, possess necessary functional groups positioned on a non-peptide scaffold to serve as "topographical" mimetics of the original peptide.

Without wishing to be bound by theory, PDAGs, portions of PDAGs, analogs of PDAGs, or mimetics of PDAGs may be activated within a target tissues producing the activated PDAG ("PDAG"). The "PDAG" moiety may then bind to specific receptor molecules in or on immune cells and/or non-immune cells as previously noted and initiate the release of cytokines such as, but not limited to, IL-6, IL-8, MCP-1, MIP-1α and β, INF-γ, TNF-α, Granzyme, and RANTES recruiting and activating macrophages, phagocytic NK cells or neutrophils and stimulating the release of other stimulatory cytokines and peptides. Cytokine release may also stimulate $CD5^+$ B-cells (also known as tissue resident B1 cells) to produce immunoglobulin (IgM, a potent opsonizing immunoglobulin) and other B-cell derived immunoglobulins such as IgA or IgG, cytokines and chemokines. Therefore, embodiments of the present invention include PDAG peptides, portions of PDAG peptides, analogs of PDAG peptides and peptide mimetics of PDAG peptides that when administered to a subject may be present in a target tissue in an inactive form (i.e. covalently attached to the lipid moiety) and activated by the action of lipoprotein lipase over time thereby allowing for the maintenance of increased PDAG peptide concentrations and immuno-activation in the target tissue of the subject over time. The sustained release of active PDAG peptide may allow for sustained innate immune system activation thereby conferring the prophylactically treated subject with an enhanced ability to fight disease when immunologically challenged over time or the therapeutically treated subject with a long acting formulation of the PDAG.

In further embodiments of the present invention, more than one PDAG peptide may be covalently conjugated to the lipid moiety. Without wishing to be bound by theory, the duration of the effective release of PDAG peptide, or peptide mimetics, may be directly related to the number of PDAG peptides, or peptide mimetics, conjugated to the lipid moiety. Therefore, administration of PDAGs, portions of PDAGs, analogs of PDAGs, or mimetics of PDAGs having three PDAG peptide moieties conjugated to a single lipid moiety may release PDAG peptide over a longer period of time than a similarly administered PDAGs, portions of PDAGs, analogs of PDAGs, or mimetics of PDAGs having only one PDAG moiety conjugated to a lipid moiety.

In some embodiments, PDAGs, portions of PDAGs, analogs of PDAGs and mimetics of PDAGs may be delivered directly to a subject, and in others, PDAGs, portions of PDAGs, analogs of PDAGs and mimetics of PDAGs may be combined with a pharmaceutically-acceptable carrier to make a pharmaceutical composition that may be delivered or provided to a subject.

A variety of administration routes are available in embodiments of the invention. The particular mode selected will depend upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous, subcutaneous, or intramuscular routes are particularly suitable for purposes of the present invention.

Pharmaceutical compositions of embodiments of the invention may include buffering agents such as, for example, acetic acid in a salt, citric acid in a salt, boric acid in a salt, phosphoric acid in a salt and the like and, optionally, preservatives, such as: benzalkonium chloride, chlorobutanol, parabens, thimerosal and the like.

Pharmaceutical compositions may conveniently be presented in unit dosage form and may be prepared by any of the methods well known in the art of pharmacy. All methods may include the step of bringing the active agent into association with a carrier that constitutes one or more accessory ingredients. In general, the compositions may be prepared by uniformly and intimately bringing the active compound into association with a liquid carrier, a finely divided solid carrier, or both, and then, if necessary, shaping the product.

Various other carrier materials may also advantageously be present in a nasal spray in appropriate quantities. The solution may be made mildly saline, by dissolving a small amount of sodium chloride in the aqueous medium. The salt concentration may be in the range of about 0.1-2.0% and will preferably be on the order of about 0.65%. Other materials such as surfactants, vitamins and vitamin derivatives, antihistamines, wetting agents, preservatives, moisturizers, emulsifiers, odorants and the like may also be present in conventional concentrations. Numerous disclosures of suitable materials may be found in the literature, along with descriptions of efficacious concentrations in aqueous media. Those skilled in the art will have no difficulty in determining suitable materials and concentrations for their known functions. Delivery of the spray to the nasal cavity may be by any conventional spray technique or device.

Embodiments of the invention also provide compositions suitable for parenteral administration wherein a sterile aqueous preparation of PDAGs, portions of PDAGs, analogs of PDAGs and mimetics of PDAGs is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid may be used in the preparation of injectables. Carrier formulation suitable for oral, subcutaneous, intravenous, intramuscular, and the like administrations can be found in Remington's Pharmaceutical Sciences, Mack Publishing Co., Easton, Pa. which is hereby incorporated by reference in its entirety.

Delivery systems of embodiments of the invention may be designed to include time-released, delayed release or sustained release delivery systems. PDAGs, portions of PDAGs, analogs of PDAGs and mimetics of PDAGs may also be used in conjunction with additional immunostimulatory or immunoenhancing agents. Using such systems, repeated administrations of PDAGs, portions of PDAGs, analogs of PDAGs and mimetics of PDAGs may be avoided increasing convenience to the subject, and may be particularly suitable for certain compositions of the present invention.

PDAGs, portions of PDAGs, analogs of PDAGs, mimetics of PDAGs and pharmaceutical compositions including PDAGs, portions of PDAGs, analogs of PDAGs and mimetics of PDAGs may be administered in an effective amount that enhances or stimulates an immune response, and in certain embodiments, in an effective amount to stimulate an innate immune response.

In general, routine experimentation in clinical trials may be used to determine specific ranges for optimal effect for each agent or pharmaceutical composition and administrative protocol. Administration of PDAGs, portions of PDAGs, analogs of PDAGs, mimetics of PDAGs and pharmaceutical compositions including PDAGs, portions of PDAGs, analogs of PDAGs and mimetics of PDAGs to specific subjects may be adjusted to within effective and safe ranges depending on the subject's condition and responsiveness to initial administrations. However, the ultimate administration protocol may be regulated according to the judgment of the attending clinician considering such factors as age, condition and size of the subject, the potency of the PDAGs, portions of PDAGs, analogs of PDAGs, mimetics of PDAGs and pharmaceutical compositions including PDAGs, portions of PDAGs, analogs of PDAGs and mimetics of PDAGs, the duration of the treatment and the severity of the disease being treated.

In embodiments of the invention, a dosage regimen of PDAGs, portions of PDAGs, analogs of PDAGs, mimetics of PDAGs and pharmaceutical compositions including PDAGs, portions of PDAGs, analogs of PDAGs and mimetics of PDAGs may be administered by nasal spray or an inhaler. For nasal spray or inhaler formulations, the ground particle size for effective dissolution or dispersion of the PDAGs, portions of PDAGs, analogs of PDAGs, mimetics of PDAGs and pharmaceutical compositions including PDAGs, portions of PDAGs, analogs of PDAGs and mimetics of PDAGs may be on the order of about 0.1 to about 20 microns, about 0.2 to about 10 microns, and in certain embodiments, about 0.2 to about 5 microns. Incorporation of PDAGs, portions of PDAGs, analogs of PDAGs, or mimetics of PDAGs into an aqueous carrier may be aided by first dispersing the PDAGs, portions of PDAGs, analogs of PDAGs, or mimetics of PDAGs in a solution such as, for example, a 4% concentration in a lactone solution. Once thoroughly mixed, dispersed, and/or dissolved, PDAGs, portions of PDAGs, analogs of PDAGs, or mimetics of PDAGs may be present at a concentration of from about 0.001% to about 2.0%, about 0.01% to about 0.35%, and in certain embodiments, about 0.10%. (All percentages herein are by weight unless otherwise noted.)

In other embodiments, PDAGs, portions of PDAGs, analogs of PDAGs, or mimetics of PDAGs may be administered orally to achieve total blood levels in the range of from about 25 μg to about 2000 μg/day, about 25 to 500 μg/day, or in certain embodiments, from about 50 to about 250 μg/day, in from two to four divided doses. In some embodiments, intermittent therapy (e.g., one week out of three weeks or three out of four weeks) may be used.

In the event that a response in a subject is insufficient at the initial doses applied, higher doses (or effectively higher doses by a different, more localized delivery route) may be employed to the extent that the patient tolerance permits. Multiple doses per day may be used to achieve appropriate systemic levels of compounds. Generally, a maximum dose may be used. A maximum dose may be considered the highest safe dose according to sound medical judgment. Those of ordinary skill in the art will understand, however, that a subject may insist upon a lower dose or tolerable dose for medical reasons, psychological reasons or for virtually any other reason.

In other embodiments of the invention, at least one PDAG, portion of PDAG, analog of PDAG, mimetic of PDAG, or PDAG peptide may be covalently attached to an antigenic peptide or simply mixed with the antigenic peptide or vaccine prior to administration of the antigenic peptide or vaccine to a subject. Without wishing to be bound by theory, the addition of PDAG or a PDAG peptide may enhance the immunogenicity of the antigenic peptide or vaccine by stimulating the innate immune system at the time of administration of the antigenic peptide or vaccine. Synthetic antigens having covalently attached one or more PDAG or PDAG peptide or PDAG or PDAG peptide antigen or vaccine admixtures may be administered to a subject to induce a long-term adaptive immune response in the subject.

In further embodiments of the invention, antibodies may be raised to naturally occurring PDAGs and PDAG peptides, and in still further embodiments, antibodies so raised may be administered to a subject to deplete the concentration of the PDAG to which the antibody was raised. Without wishing to be bound by theory, administration of PDAG and/or PDAG peptide depleting antibodies may be a beneficial therapeutic strategy for subjects exhibiting uncontrolled systemic inflammation such as, for example, sepsis, atherosclerosis, rheumatoid diseases, autoimmune diseases, inflammatory bowel disease, Type I diabetes and the like. In similar embodiments, PDAG and PDAG peptide depleting antibodies may be used to treat non-septic injury such as, for example, trauma, inflammation due to extensive surgical procedures and the like.

Antibodies to PDAG and PDAG peptides, of embodiments of the invention, may be raised in rabbits, mice, goats, horses, or other species by methods well known to those skilled in the art. For example, monoclonal antibodies to PDAG or PDAG peptides may be raised utilizing the hybridoma fusion techniques, and selected hybridomas may be maintained in cell culture or in a bioreactor for the continuous production of monoclonal antibodies. In some embodiments, the PDAG peptide specific binding region of a monoclonal antibody may be selectively produced by specific chemical cleavage of the whole antibody or recombinant methods known in the art. In other embodiments, the specific PDAG binding region may be conjugated to the Fc region of a human antibody to produce a humanized chimera for administration of a PDAG depleting antibody to human subjects. Chimeric antibodies are well known in the art and may be produced using synthetic, semi-synthetic, or recombinant methods. Humanized PDAG chimera antibodies may be advantageous for use in human subjects since substantially no secondary antibody reaction in human subjects may be caused.

In still other embodiments of the invention, fluorescently labeled PDAGs, PDAG peptides, or PDAG antibodies may be made. In such embodiments, fluorescent dyes such as, but not limited to, phycoerythrin (PE), a red fluorescing dye, and fluorosceinisothiocynate (FITC), a green fluorescing dye, may be activated conjugated to the N-terminus of the peptidyl portion of PDAG, a free sulfhydryl or amino or carboxyl in the PDAG peptide, or a free amino group of a PDAG antibody.

Methods for making such conjugates are well known in the art for example, a PDAG or PDAG peptide may be conjugated to a fluorescent dye through its N-terminus by activating the peptide by attaching a thiol reactive extended-chain analogue of succinimidyltrans-4-(maleimidylmethyl) cyclohexane-1-carboxylate(LC-SMCC) and separating unreacted LC-SMCC from the derivatized PDAG peptide by size exclusion chromatography. The pyridyldisulfide derivative of R-PE or FITC to the free thiol may by activated by incubating the R-PE or FITC for 10 to 15 minutes in tris-(2-carboxyethyl)phosphine (TCEP). The purified LC-SMCC-PDAG peptide derivative may then be combined with activated R-PE or FITC and mixed at 4° C. overnight. The reaction may be stopped by the addition of N-ethylmaleimide (NEM) which caps any remaining thiol groups. The R-PE or FITC-PDAG conjugate may be purified by size exclusion chromatography and lyophilized to yield the final product.

In other embodiments of the invention, fluorescently labeled PDAGs or PDAG peptides may be used to analysis tissue samples. For example, fluorescently labeled PDAGs or PDAG peptides may be mixed ex vivo with samples of a subject to detect and quantitate immune cells engaging the fluorescently labeled PDAGs or PDAG peptides. In still other embodiments, fluorescently labeled antibodies to the PDAGs or PDAG peptides may be used to detect and quantitate the levels of PDAG or PDAG peptide in ex vivo samples from subjects using methods such as fluorescent microscopic methods, ELISA and the like. Such methods of analysis are well known to those practiced in the art.

Example 1

This example describes the isolation and structural analysis of the PDAG in the present invention. PDAGs may be routinely isolated in research scale quantities from the serum fraction of coagulated blood by dialysis against distilled water through a 7-10 kDa molecular weight cut-off dialysis cassette (Slide-A-Lyzer, Pierce Biotechnology, Inc.) and concentration by in vacuo evaporation and lyophilization of the dialysate.

The crude serum fraction is further purified by size exclusion chromatography or filtration by passage through a size exclusion resin or filter to remove salts and other low molecular weight contaminants Final purification is accomplished by organic solvent extraction and reversed phase HPLC. This procedure provides sufficient material after purification to conduct biological activity studies and initiate the chemical characterization of the bioactive component(s). LC/MS analysis characterizes the PDAG component as a 2-3 kDa lipopeptide. Quantitative analysis based upon the total mass abundance indicates that PDAG purity is >98% after HPLC. HPLC/ESI tandem mass spectrometry may be used to confirm the amino acid sequence of the peptide and identify the lipid portion of the PDAG in the present invention. A representative HPLC profile of purified non-primate PDAG is depicted in FIG. 1. HPLC chromatography was performed on an Ultimate 3000 HPLC (Dionex, Sunnyvale, Calif.). The column was a Zorbax C8 1×150 mm (Agilent, Santa Clara, Calif.). 200 ul of the sample, in water, was injected into a 200 ul loop. The gradient was a 5-65% solvent A to solvent B over 60 minutes, followed by a 5 minutes wash with 90% solvent B. Solvent A was 5% acetonitrile+0.1% TFA and solvent B was 90% acetonitrile+ 0.1% TFA at a flow rate of 50 ul/min. Detection was at 214 nm and 280 nm.

Figure 1B:
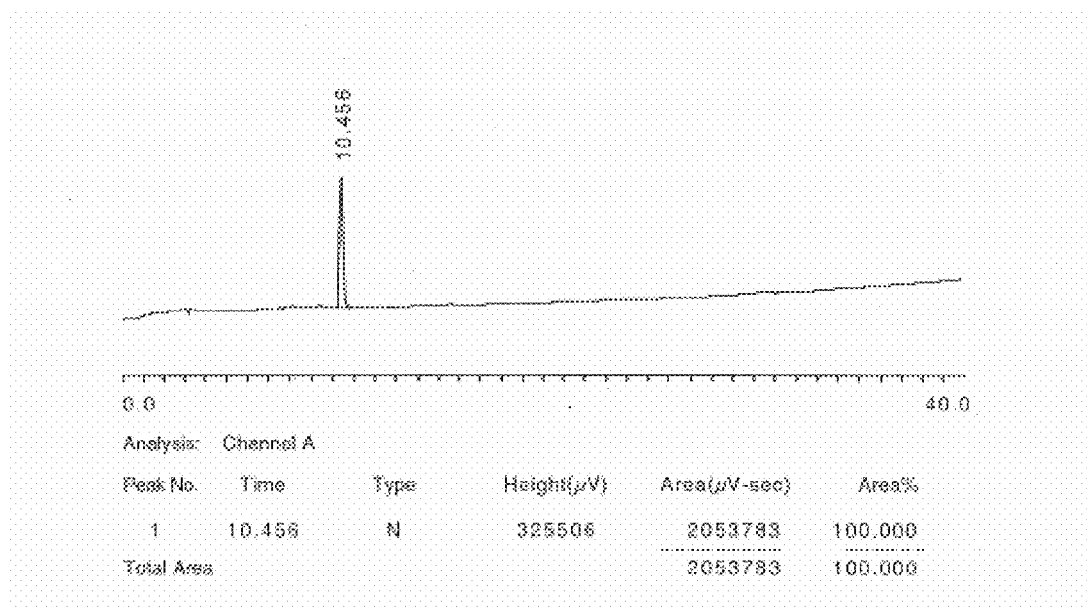

Caprine serum (2 L) was extracted to yield approximately 100 μg of purified PDAG. FIG. 1A is a representative chromatogram of the methanol:chloroform soluble fraction (Technical Grade PDAG). The peak eluting at nominally 10.4 minutes was determined to be the parent PDAG and the peaks eluting between nominally 9.4 minutes and 4.8 minutes are hydrolysis products of the parent PDAG. The peak eluting at 2.9 minutes was characterized as containing mainly oligosaccharides (data not shown). The purified PDAG (10.4 minute peak) was collected by preparative reversed phase chromatography and the solvent was removed in vacuo. These results are depicted in FIGS. 1A and 1B Example 2

This example describes the structural elucidation of native PDAG. Edman degradation sequence analysis of the purified PDAG identified an amino acid sequence of ($X_1$)LYDK-GYTSKEQKDCVGI($X_2$) and a calculated molecular weight of 1883.57 amu for the putative PDAG peptide. $X_1$ and $X_2$ were unidentified derivatized amino acids or non-amino acid prosthetic groups. Liquid chromatography/tandem mass spectrometry (LC/MS.sup.n) was utilized to analyze purified PDAG to (a) identify the N-terminal and C-terminal prosthetic groups and (b) confirm the amino acid sequence of the peptide. ESI-MS of the PDAG parent peak (10.4 minutes) revealed 3 major ion fragments. The most abundant (Fragment A) was determined to be tryptophan (m/z 205) that co-eluted with PDAG as a PDAG-tryptophan adduct.

Figure 2A:
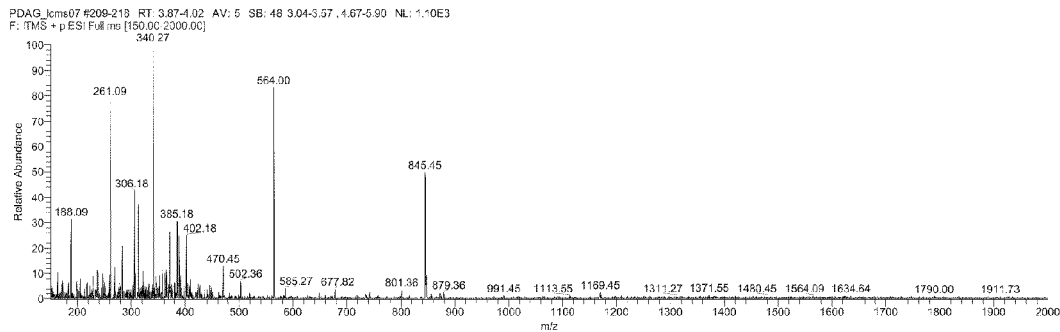
FIG. 2 shows the ESI mass spectrum of a fragment from caprine derived PDAG (FIG. 2A) and an MS/MS mass spectrum of multi-charged ion species (m/z 845.45) confirming the amino acid sequence of the present invention (FIG. 2B).
Figure 2B:
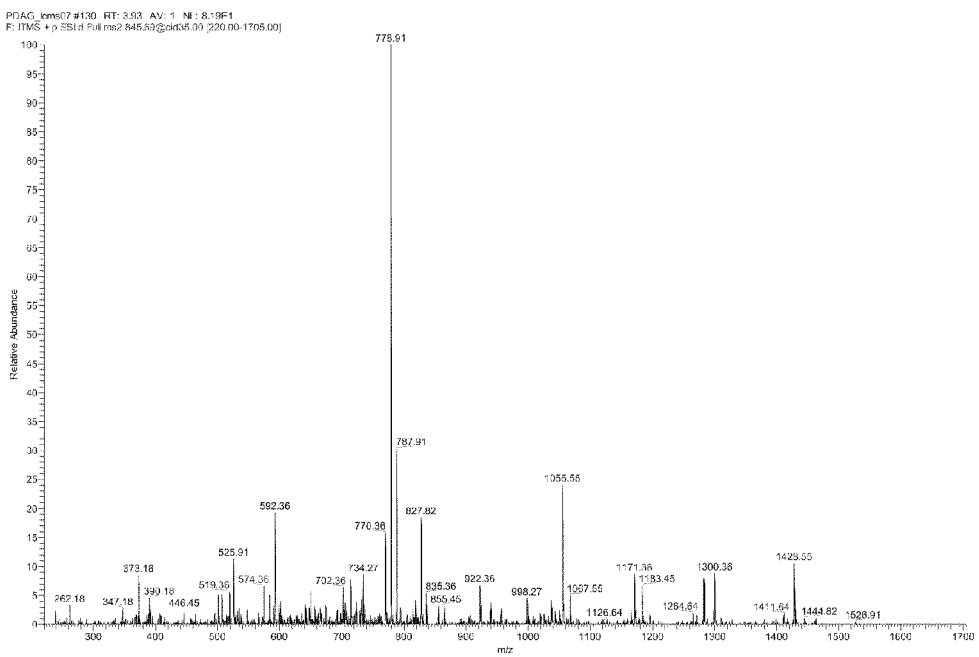

The mass spectrum of the second most abundant ion, Fragment B (MW 1688.8), had two multi-charged ions. The ion at m/z 564.00 is $[M+3H]^{3+}$ and the ion at 845.45 is $[M+2H]^{2+}$. The MS/MS product ion mass spectrum of the m/z 845.5 ion had the amino acid sequence acALYDK-GYTSKEQKD (SEQ ID NO:3) (m/z 1688.8). This sequence is consistent with the first 13 amino acids from the Edman degradation sequence analysis where $X_1$ is N-acetyl alanine (acA). The mass spectra for Fragment B are presented in FIGS. 2A and 2B.

As further experimental evidence for the structure assigned to PDAG a series of MALDI-TOF mass spectrometry experiments were conducted. Because PDAG was isolated as a Tryptophan:PDAG adduct (200:1 estimated) PDAG was analyzed by MALDI-TOF MS with and without added matrix. No molecular ion corresponding to the intact PDAG molecule was observed, however, four major ion fragments accounting for the entire PDAG molecule were detected in the positive ion spectrum without added matrix (the tryptophan served as a matrix). The high mass fragment (m/z 1282.71) arises from the loss of neutral NH.sub.3 from the N-terminal fragment ion [acALYDKGYTSKE]+ (SEQ ID NO:4). The low mass fragment (m/z 1133.30) is consistent with the y-ion containing the C-terminal diacylglycerol ("DAG") [DCVGI-(DAG)]+ (SEQ ID NO:5). The base peak (m/z 1208.47) is consistent with a tryptophan adduct of the internal z-ion fragment [KEQKDCVGI]W(SEQ ID NO:6). The corresponding y-ion (+15 amu) is observed at m/z 1223.61. The y-ion at m/z 1207.53 is C-terminal fragment [TSKEQKDCVGI]+ (SEQ ID NO:7).

Figure 3:
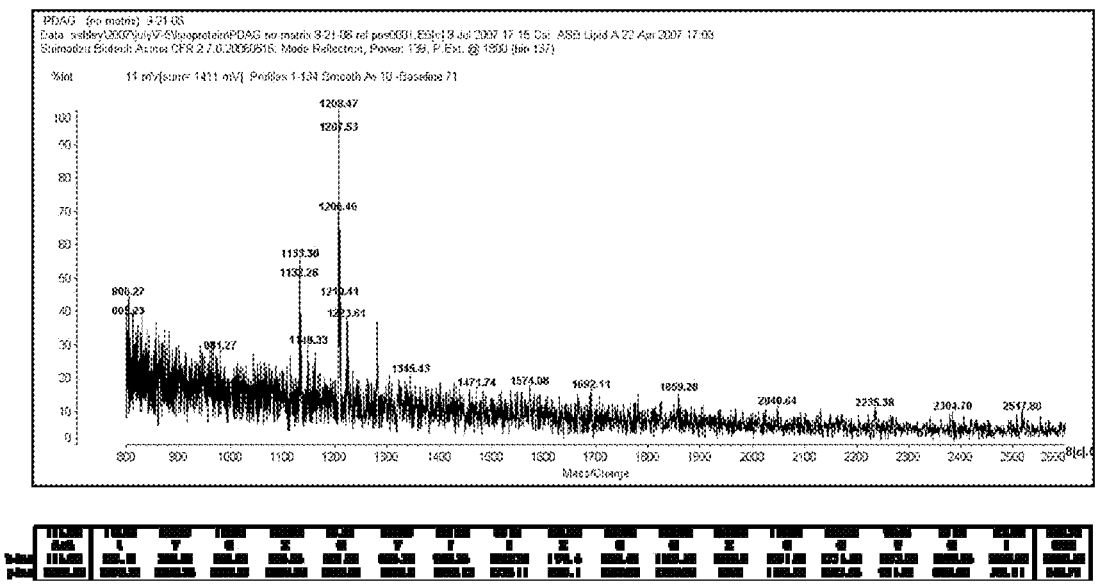
FIG. 3 shows the PSD MALDI-TOF mass spectrum of purified PDAG in a dihydroxybenzoic acid matrix.

Co-crystallization of the Tryptophan:PDAG adduct with dihydroxybenzoic acid (DHB) and reanalysis by MALDI-TOF mass spectrometry gave an expanded series of ion fragments that also accounted for the entire structure of PDAG (FIG. 3).

The serum derived PDAG product is especially labile to hydrolysis under acidic conditions and this may account for the difficulties in obtaining a molecular ion under either ESI or MALDI ionization conditions. The peaks eluting between 4.83 and 9.36 minutes in FIG. 1A are hydrolysis products of the parent PDAG peak eluting at 10.42 minutes (data not shown). Therefore, purified PDAG was subjected to mild acid hydrolysis, in situ N-terminal sulfonation followed by analysis of the hydrolysis products to account for the entire PDAG structure. The PSD MALDI-TOF analysis of the N-terminal sulfonated peptide fragments that were generated after mild acid hydrolysis of PDAG showed multiple y-ions consistent with previously observed peptide fragments and accounted for the complete structure of PDAG (FIG. 4). Thus, the putative PDAG structure acALYDK-GYTSKEQKDCVGI-DAG (SEQ ID NO:8) is consistent with the Edman degradation sequence analysis, the ESI-MS/MS sequence analysis, and the PSD MALDI-TOF MS analyses of the natural product.

Given the putative sequence for the peptide in PDAG, the non-redundant sequence database was searched for homologous sequences using the NCBI BLAST search tool BLASTP (Altshul, 1997). The PDAG peptide has identical sequence homology to the internal sequence of amino acids at positions 558-574 in the transient receptor potential channel-related protein 1 (TRPC1). No significant homology with other known proteins or peptides was noted. A comparison of the amino acid sequence at positions 557-574 from bovine, mouse, and human TRPC1 with the putative PDAG peptide sequence revealed identical amino acid sequences except that the 9-serine in bovine PDAG was replaced by proline.

Example 3

The pDAG peptide was synthesized by a standard solid phase synthesis protocol with extended HBTU coupling on H-Isoleucine-2-Chlorotrityl resin using an AAPPTEC 348 Sigma (Advanced Automated Peptide Protein Technologies, Inc., Louisville, Ky.) peptide synthesizer. The fully protected peptide sequence conjugated to the resin [Ala-Leu-Tyr(But)-Asp (OBut)-Lys(Boc)-Gly-Tyr(But)-Thr(But)-Ser(But)-Lys (Boc)-Glu(OBut)-Gln(Trt)-Lys(Boc)-Asp(OBut)-Cys(Trt)-Val-Gly-Ile-RESIN] was recovered after washing with dichloromethane. The peptide conjugated resin was acetylated at the N-terminal alanine of the peptide by the addition of 10% acetic anhydride in N,N-diisopropylethylamine (20%) and N,N-dimethylacetamide (70%). After two hours at room temperature the resin was filtered, washed successively with N,N-dimethylacetamide and dichloromethane, and lyophilized. The acetylated and fully protected peptide was cleaved from the resin using 20 ml of a 1:4 solution of 1,1,1,3,3,3-hexafluoro-2-propanol in dichloromethane. After two hours at room temperature, the resin was filtered and washed with 2 ml of the cleavage solution. The filtrate was evaporated in vacuo using a rotary evaporator. A sample was analyzed by mass spectrometry to confirm the expected mass at m/z 3286 (data not shown).

1-Stearoyl-2-arachidonoyl-sn-glycerol (Sigma Aldrich) was conjugated to the C-terminal isoleucine carboxyl of the fully protected acetylated peptide using the dicyclohexyl-carbodiimide/dimethylaminopyridine (DCC/DMAP) coupling reaction. 1-stearoyl-2-arachidonoyl-sn-glycerol (5 mg) was dissolved in 2 ml of dichlormethane and mixed with 2 equivalents of the fully protected acetylated peptide dissolved in 2 ml of dichloromethane and 1 equivalent of DMAP also dissolved in 2 ml of dichloromethane. The reaction was allowed to proceed overnight at room temperature. The reaction mixture was dried in vacuo and the protecting groups were removed in situ by the addition of 8 ml of the deprotection solution (2.5% 1,2-ethandiol, 94% trifluoroacetic acid, 0.1% triisopropylsilane, and 2.5% water). After a two hour incubation period at room temperature in the presence of the deprotecting solution the reaction mixture was filtered and the filtrate was evaporated in vacuo on a rotary evaporator.

Purification of the crude product was accomplished by reversed-phase preparative scale HPLC using a Jupiter® Proteo (Phenomenex, Inc., Torrance, Calif.) column and a binary mobile phase gradient (Solvent A: 0.1% TFA in water Solvent B: 0.1% TFA in acetonitrile) formed from 5% to 95% Solvent B over 20 minutes (4.5% per minute) at a flow rate of 1 ml/minute and the effluent was continuously monitored at 220 nm. The pDAG product eluted at 22.9 minutes under these conditions. The crude product (63 mg) was dissolved in 4 ml of acetonitrile and 2 ml of water and loaded onto the preparative scale column. The peak eluting at 22.9 minutes was collected in 22.5 ml of the mobile phase (95% acetonitrile/0.1% TFA). The effluent was evaporated in vacuo and the final mass of pDAG peptide was measured to be 2.5 mg (4% yield) with a purity as determined by HPLC analysis to be 98.9%.

Example 4

Figure 5:
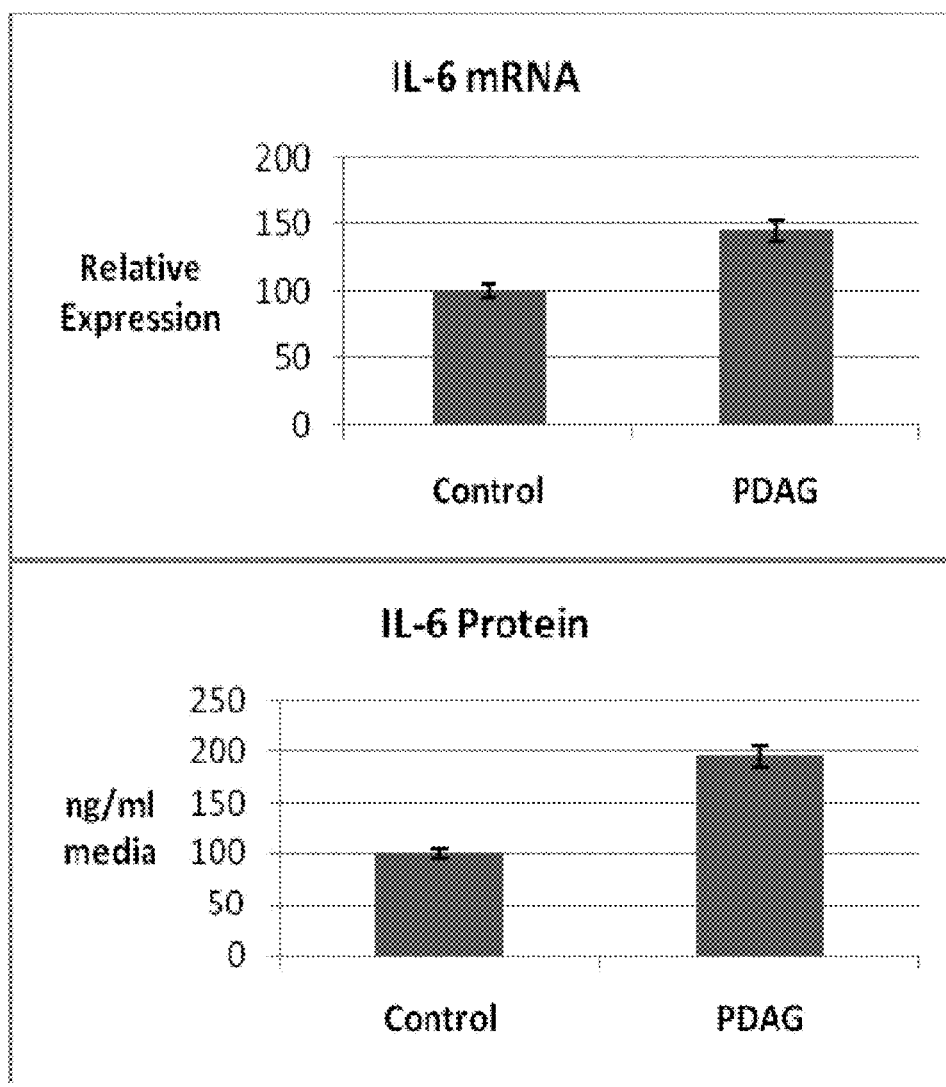
FIG. 5 shows stimulation of IL-6 mRNA and IL-6 protein expression in fibroblasts that have been incubated with PDAG.

Fibroblasts were stimulated with synthetic PDAG for 24 h. RNA was extracted from the fibroblasts and IL-6 transcripts were measured by real-time PCR and IL-6 protein was measure in the media by ELISA. We found that 100 pg/ml of PDAG stimulated fibroblasts to increase IL-6 mRNA levels compared to the control (untreated cells), P=0.001. Likewise approximately 2-fold more IL-6 protein in the media of the PDAG treated fibroblasts (P=0.0001) was measured. These results are presented in FIG. 5.

Figure 6:
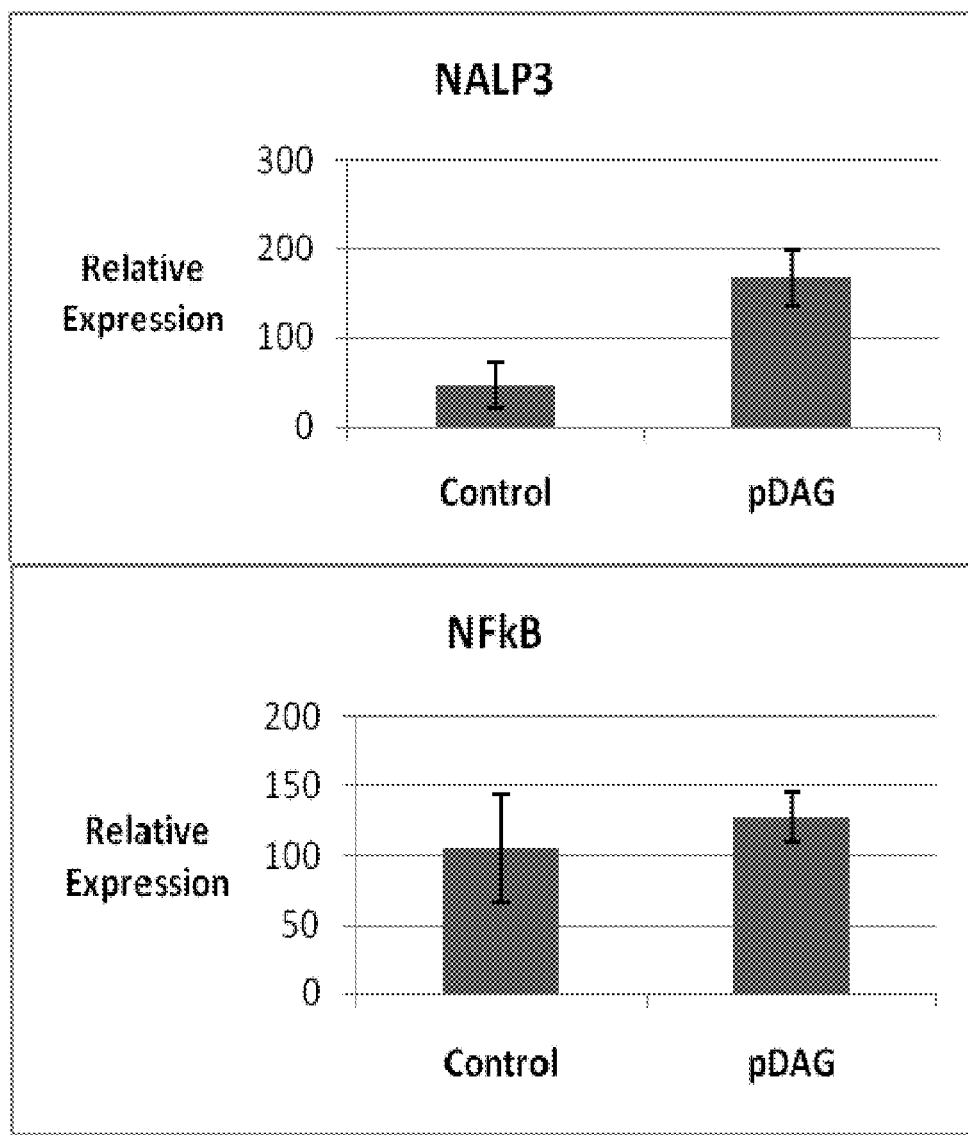
FIG. 6 shows that PDAG stimulates NALP3 mRNA expression in fibroblasts but not NFκB.

Example 5 mRNA was extracted from primary human fibroblasts incubated overnight with 100 pg/ml synthetic PDAG. NALP3 and NFκB transcripts were measured. NALP3 transcripts were found to increase 1.75 fold (P=0.007), whereas NFκB transcripts did not (P=0.4). These results are presented in FIG. 6.

Example 6

Figure 7:
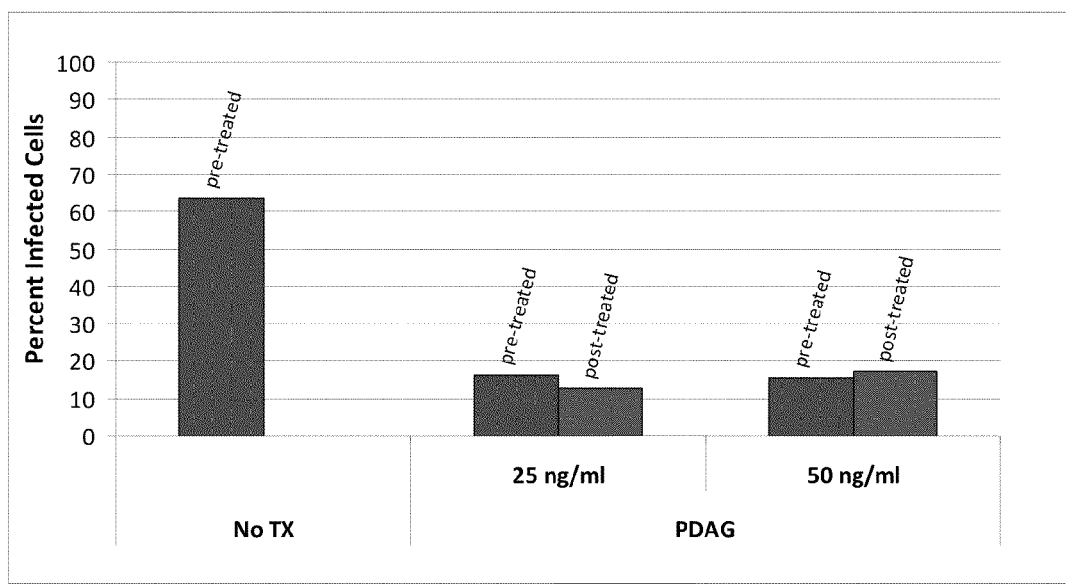
FIG. 7 shows that both PDAG and the PDAG peptide (25 ng/ml and 50 ng/ml) induce *Chlamydia pneumoniae* clearance from infected monocytes.
Figure 8:
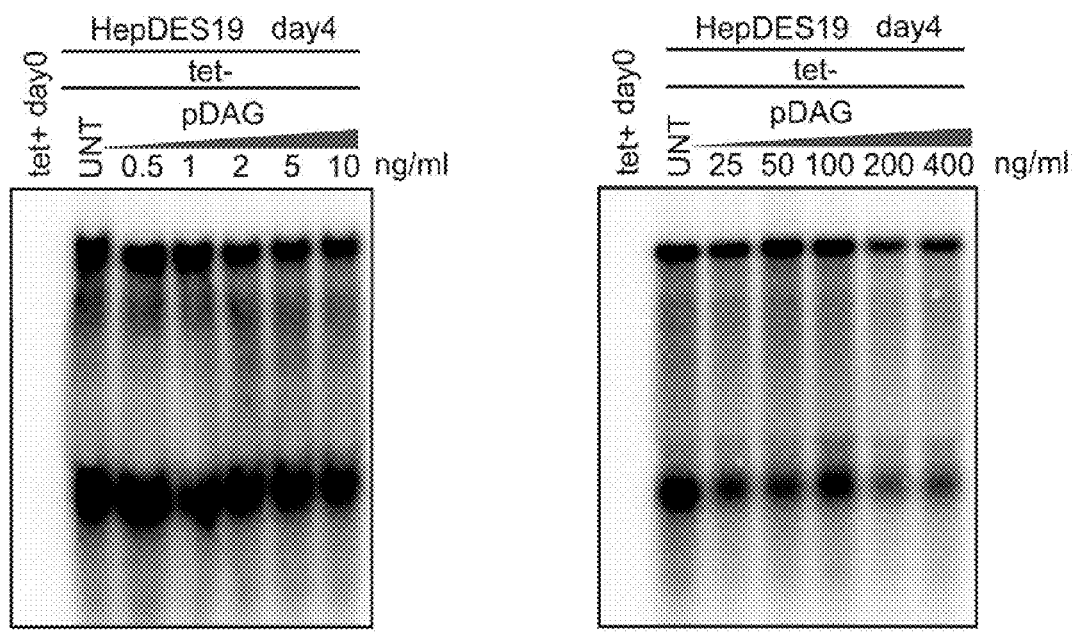
FIG. 8 shows that PDAG suppresses Hepatitis B virus replication in HepDES 19 cells.
Figure 9:
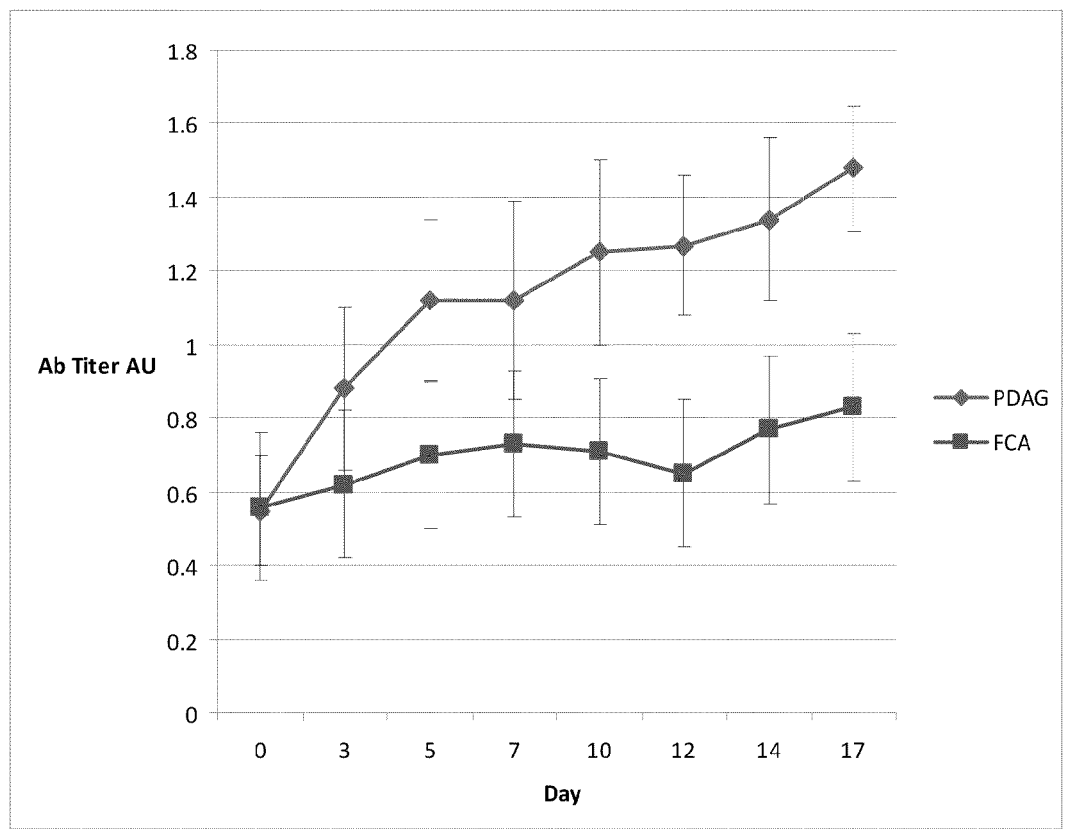
FIG. 9 shows that PDAG induces a two-fold increase in antigen specific IgM production in rabbits inoculated with heat killed *M. tuberculosis* (FCA).
Figure 10:
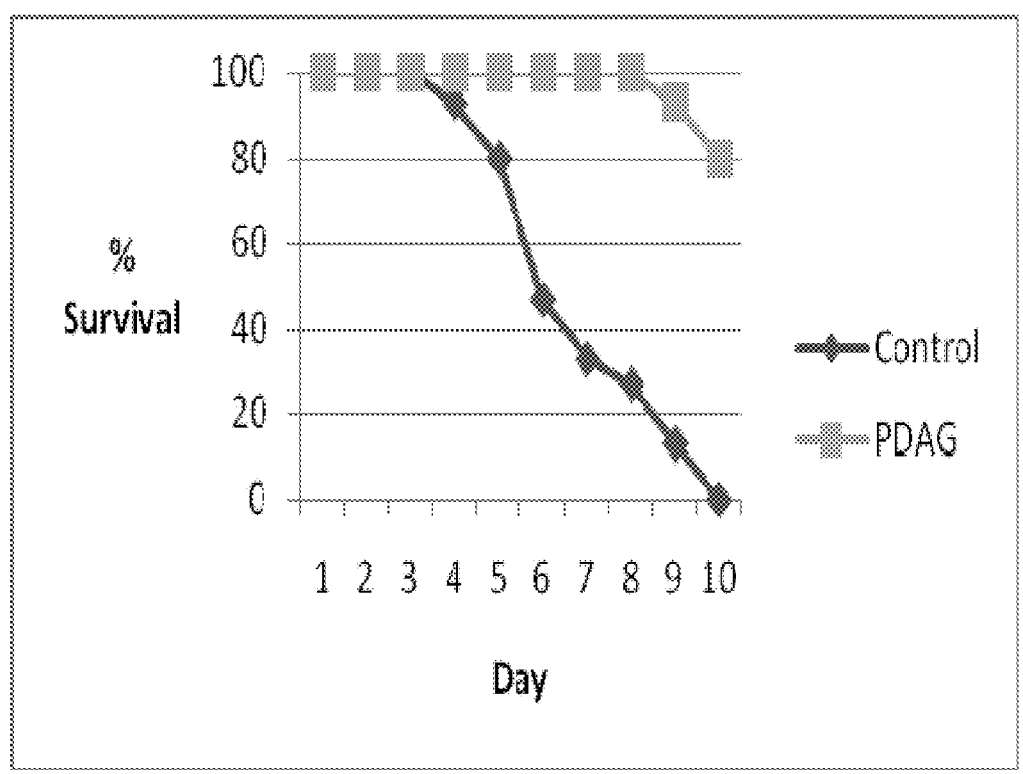
FIG. 10 shows that PDAG administration significantly delays disease progression in mice infected with a lethal dose of *Salmonella typhimurium*.

THP-1 monocytes ($5 \times 10^4$ cells/well) were cultured in Hank's Buffered Saline 1 with 10% FBS in a 24-well microplate. Cells were infected with $2.5 \times 10^4$ AR39 *Chlamydia pneumoniae* (CPn) bacteria cells to give an MOI=1 and the infected cells were maintained for 72 hours after infection with a daily media change. Cells were either treated with the PDAG vehicle (0.01% Tween-20 in DMSO) or PDAG (25 ng/ml and 50 ng/ml) 24 hours prior to infection or 24 hours after infection. After the 72 hour incubation period cells were harvested and permeabilized with Cytofix/Cytoperm (BD Pharmingen) and mouse α-CPn monoclonal IgG (clone 61C75) was added and the permeabilized cells incubated for 1 hour. After incubation cells were washed and FITC labeled α-mouse IgG was added and incubated for 1 hour. Cells were again harvested and washed. Quantitation of infected cells was measured by flow cytometry. The viability of cells was determined by trypan blue exclusion. These results are presented in FIG. 7.

Example 7

A tetracycline inducible HBV-stable cell line, HepDES19 cells (Guo, 2007), were maintained in DMEM/F-12 medium with penicillin and streptomycin (Invitrogen), 10% FBS, 500 µg/ml G418 (Invitrogen) and 1 µg/ml tetracycline (Sigma-Aldrich, St. Louis, Mo.). To initiate the HBV replication in HepDES19 cells, tetracycline was withdrawn from the medium and the cell was cultured for 4-5 days before viral DNA analysis. To treat the cells with pDAG, the peptide was added in the tetracycline free medium and supplied on the cell culture daily. The concentration of solvent DMSO was adjusted to 0.01% in every treatment.

HBV core DNA was extracted from pDAG-treated HepDES19 cells as described previously (Guo, 2009). Briefly, cells from one 35 mm dish were lysed with 0.5 ml of lysis buffer (10 mM Tris-HCl pH 8.0, 10 mM EDTA, 1% NP40 and 2% sucrose) at 37° C. for 10 minutes. Cell debris and nuclei were removed by centrifugation and the supernatant was mixed with 130 l of 35% polyethylene glycol (PEG-8000) containing 1.5 M NaCl. After 1 hour incubation in ice, viral nucleocapsids were pelleted by centrifugation at 10,000 rpm for 5 min at 4° C., followed by 1 hour digestion at 37° C. in 200 µl of digestion buffer [0.5 mg/ml pronase (Calbiochem), 0.5% SDS, 150 mM NaCl, 25 mM Tris-HCl pH 8.0, and 10 mM EDTA]. The digestion mixture was extracted twice with phenol, and DNA was precipitated with ethanol and dissolved in TE buffer (10 mM Tris-HCl, pH 8.0, 1 mM EDTA). The DNA sample was resolved by electrophoresis into a 1.5% agarose gel. Gel was then subjected to depurination in 0.2 N HCl for 10 min at room temperature, then denaturation in a solution containing 0.5 M NaOH and 1.5 M NaCl for 1 hr, followed by 1 hr neutralization in a buffer containing 1 M Tris-HCl (pH7.4) and 1.5 M NaCl. DNA was then blotted onto Hybond-XL membrane (GE Healthcare) in 20×SSC buffer. Membranes were probed with an α-$^{32}$P-UTP (800 Ci/mmol, Perkin Elmer)-labeled HBV minus strand-specific full-length riboprobe. Hybridization was carried out in 5 ml EKONO hybridization buffer (Genotech) with 1 hr pre-hybridization at 65° C. and overnight hybridization at 65° C., followed by a 1 hr wash with 0.1×SSC and 0.1% SDS at 65° C. The membrane was exposed to a phosphorimager screen and hybridization signals were revealed and quantified with QuantityOne software (Bio-Rad).

Example 8

Female New Zealand White rabbits were inoculated with FCA with (n=3) and without (n=3) native PDAG. Blood samples were drawn one day prior to inoculation (background) and again on days 3, 5, 7, 10, 12, 14, and 17 post-inoculation. Sera were analyzed in triplicate for *M. tuberculosis* IgM production by ELISA. The antibody titers for each day post-inoculation were background subtracted using the day −1 titer. By post-inoculation day 5 the IgM titer in the rabbits inoculated with FCA+PDAG were significantly greater than the titers in the rabbits receiving FCA only (P=0.0004). These results are depicted in FIG. 9.

Example 9

Swiss Webster mice were challenged with a lethal dose, $5\times10^3$ cfu/mouse of *Salmonella typhimurium*. Fifteen of the mice were treated with 5 μg/ml PDAG 24 hours prior to the lethal inoculation. Mice were maintained and monitored daily for 10 days. Mortality was observed in the control group on day 4 but not in the PDAG treated group until day 7. By day 10, 12 mice in the PDAG treated group remained alive, whereas all had died in the untreated group. P<0.0001. These results are depicted in FIG. 10.

Although the present invention has been described with reference to specific embodiments, workers skilled in the art will recognize that many variations may be made therefrom, for example in the particular experimental conditions herein described, and it is to be understood and appreciated that the disclosures in accordance with the invention show only some preferred embodiments and objects and advantages of the invention without departing from the broader scope and spirit of the invention. It is to be understood and appreciated that these discoveries in accordance with this invention are only those which are illustrated of the many additional potential applications of the compound that may be envisioned by one of ordinary skill in the art, and thus are not in any way intended to be limiting of the invention. Accordingly, other objects and advantages of the invention will be apparent to those skilled in the art from the detailed description together with the claims.

SEQUENCE LISTING

| Number | Seq. I.D. Number | Nucleotide Sequence |
|---|---|---|
| 1 | SEQ. ID NO: 1 | Xaa Leu Tyr Asp Lys Gly Tyr Thr Ser Lys Glu Gln Lys Asp Cys Val Gly Ile Xaa |
| 2 | SEQ. ID NO: 2 | Xaa Leu Tyr Asp Lys Gly Tyr Thr Pro Lys Glu Gln Lys Asp Cys Val Gly Ile Xaa |
| 3 | SEQ. ID NO: 3 | acAla Leu Tyr Asp Lys Gly Tyr Thr Ser Lys Glu Gln Lys Asp |
| 4 | SEQ. ID NO: 4 | acAla Leu Tyr Asp Lys Gly Tyr Thr Ser Lys Glu |
| 5 | SEQ. ID NO: 5 | Asp Cys Val Gly Ile Xaa |
| 6 | SEQ. ID NO: 6 | Lys Glu Gln Lys Asp Cys Val Gly Ile Trp |
| 7 | SEQ. ID NO: 7 | Thr Ser Lys Glu Gln Lys Asp Cys Val Gly Ile |
| 8 | SEQ. ID NO: 8 | acAla Leu Tyr Asp Lys Gly Tyr Thr Ser Lys Glu Gln Lys Asp Cys Val Gly Ile |
| 9 | SEQ. ID NO: 9 | Thr Ser Lys Glu Gln Lys Asp Cys |
| 10 | SEQ. ID NO: 10 | Gly Tyr Thr Ser Lys Glu Gln Lys |

SEQUENCE LISTING

| Number | Seq. I.D. Number | Nucleotide Sequence |
|---|---|---|
| 11 | SEQ. ID NO: 11 | acAla Leu Tyr Asp Lys Gly Tyr Thr |
| 12 | SEQ. ID NO: 12 | Thr Ser Lys Glu Gln Lys Asp |
| 13 | SEQ. ID NO: 13 | Lys Glu Gln Lys Asp Cys Val |
| 14 | SEQ. ID NO: 14 | acAla Leu Tyr Asp Lys Gly Tyr |
| 15 | SEQ. ID NO: 15 | Ser Lys Glu Gln Lys Asp |
| 16 | SEQ. ID NO: 16 | Lys Asp Cys Val Gly Ile |
| 17 | SEQ. ID NO: 17 | Lys Glu Gln Lys Asp |
| 18 | SEQ. ID NO: 18 | Gln Lys Asp Cys Val |

I claim:

1. A synthetic peptide comprising the amino acid sequence selected from (SEQ ID NO:1) and (SEQ ID NO:2), wherein Xaa is selected from the group consisting of a naturally occurring amino acid, absent, a derivatized amino acid, a non-amino acid prosthetic group and combinations thereof and wherein said amino acid sequence is linked to a diacylglycerol.

2. The synthetic peptide of claim 1 wherein the N-terminal X is Q.

3. The synthetic peptide of claim 1 wherein the N-terminal X is N-acetyl alanine.

4. A compound having the general formula (I):

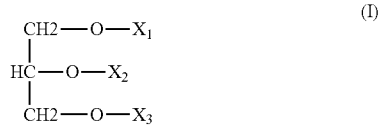

wherein at least one $X_1$, $X_2$ and/or $X_3$ is a synthetic peptide comprising the amino acid sequence selected from (SEQ ID NO:1) and (SEQ ID NO:2), wherein Xaa is selected from the group consisting of a naturally occurring amino acid, absent, a derivatized amino acid, a non-amino acid prosthetic group and combinations thereof and wherein any remaining $X_1$, $X_2$ and/or $X_3$ is selected from group consisting of hydrogen, $C_2$ to $C_{25}$ fatty acid, and combinations thereof.

5. A pharmaceutical composition comprising the peptide of claim 1.

6. The pharmaceutical composition of claim 5 having a pharmaceutically acceptable buffering agent or a physiologically acceptable carrier.

7. The pharmaceutical composition of claim 6 wherein said buffering agent is from a group consisting of acetic acid in a salt, citric acid in a salt, boric acid in a salt, phosphoric acid in a salt and combinations thereof.

8. The pharmaceutical composition of claim 6 wherein said carrier formulation is from a group suitable for oral, subcutaneous, intravenous, intramuscular, intraperitoneal, buccal or ocular route, rectally, parenterally, intrasystemically, intravaginally, topically, orally as an oral or nasal spray, and combinations thereof.

9. The pharmaceutical composition of claim 5 where said pharmaceutical composition is in the form of a pill, tablet, lozenge, coated tablet, granule, capsule, hard or soft gelatin capsule, aqueous solution, alcoholic solution, oily solution, syrup, emulsion, suspension, pastille, suppository, solution for injection, ointment, tincture, cream, lotion, powder, spray, transdermal therapeutic systems, nasal spray, aerosol mixture, microcapsule, implant, rod or plaster.

10. The pharmaceutical composition of claim 8 wherein said parenteral formulation contains wetting agents, suspending agents, diluents, solvents, or combinations thereof.

11. The pharmaceutical composition of claim 10 wherein said diluent is 1,3-butanediol.

12. The pharmaceutical composition of claim 10 wherein said solvent is from a group consisting of water, Ringer's solution, isotonic sodium chloride solution, and sterile fixed oils.

13. The pharmaceutical composition of claim 12 wherein said fixed oil is a bland fixed oil.

14. The pharmaceutical composition of claim 9 wherein said solution for injection contains fatty acids.

15. The pharmaceutical composition of claim 5 having a preservative.

16. The pharmaceutical composition of claim 15 wherein said preservative is from the group containing benzalkonium chloride, chlorobutanol, parabens, thimerosal and combinations thereof.

17. The pharmaceutical composition of claim 8 where said carrier provides a mild saline solution in said nasal spray.

18. The pharmaceutical composition of claim 17 where said saline solution is about 0.1% to 2.0%.

19. The pharmaceutical composition of claim 17 where said saline solution is about 0.65%.

20. The pharmaceutical composition of claim 8 where said spray formulation has a ground particle size for effective dispersion of said compound.

21. The pharmaceutical composition of claim 20 where said particle size is about 0.1 to 20 microns.

22. The pharmaceutical composition of claim 20 where said particle size is about 0.2 to 10 microns.

23. The pharmaceutical composition of claim 20 where said particle size is about 0.2 to 5 microns.

24. The pharmaceutical composition of claim 5 containing additives from a group consisting of surfactants, vitamins, vitamin derivatives, antihistamines, wetting agents, preservatives, moisturizers, emulsifiers, odorants, and combinations thereof.

25. A pharmaceutical delivery system comprising:
    a. pharmaceutical composition of claim 5; and
    b. a release means from a group consisting of time-released, delayed release, sustained release, and combinations thereof.

26. A method for preparing the pharmaceutical composition of claim 5 comprising:
    a. obtaining the peptide of claim 1; and
    b. uniformly incorporating the peptide with a carrier wherein said carrier contains one or more accessory ingredients, said carrier being either a liquid or solid.

27. A method for enhancing the immunogenicity of a vaccine comprising administering the pharmaceutical composition of claim 5 and the vaccine to a subject.

28. A method for synthesizing PDAG comprising,
    a. synthesizing the peptide of claim 1 by a solid-phase method wherein said synthesizing does not have a de-protection step;
    b. activating a C-terminal carboxylic acid;

c. incubating with DAG and a catalytic agent wherein said incubation produces PDAG; and d. cleaving peptide side chain protective groups with Reagent K.

29. The method of claim 28 wherein said activating is with dicyclohexylcarbodiimide.

30. The method of claim 28 wherein said catalytic agent is dimethylaminopyridine.

31. The method of claim 28 where PDAG is purified by chromatography.

* * * * *

SEQUENCE LISTING

<160> NUMBER OF SEQ ID NOS: 18

<210> SEQ ID NO 1
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: Xaa can be a naturally occurring amino acid,
      absent, a derivatized amino acid, a non-amino acid prosthetic
      group and combinations thereof
<220> FEATURE:
<221> NAME/KEY: MISC_FEATURE
<222> LOCATION: (19)..(19)
<223> OTHER INFORMATION: Xaa can be a naturally occurring amino acid,
      absent, a derivatized amino acid, a non-amino acid prosthetic
      group and combinations thereof

<400> SEQUENCE: 1

Xaa Leu Tyr Asp Lys Gly Tyr Thr Ser Lys Glu Gln Lys Asp Cys Val
1               5                   10                  15

Gly Ile Xaa

<210> SEQ ID NO 2
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (1)..(1)
<223> OTHER INFORMATION: Xaa can be a naturally occurring amino acid,
      absent, a derivatized amino acid, a non-amino acid prosthetic
      group and combinations thereof
<220> FEATURE:
<221> NAME/KEY: MISC_FEATURE
<222> LOCATION: (19)..(19)
<223> OTHER INFORMATION: Xaa can be a naturally occurring amino acid,
      absent, a derivatized amino acid, a non-amino acid prosthetic
      group and combinations thereof -continued

<400> SEQUENCE: 2

Xaa Leu Tyr Asp Lys Gly Tyr Thr Pro Lys Glu Gln Lys Asp Cys Val
1               5                   10                  15

Gly Ile Xaa

<210> SEQ ID NO 3
<211> LENGTH: 14
<212> TYPE: PRT
<213> ORGANISM: Artificial Sequence
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION

<400> SEQUENCE: 3

Ala Leu Tyr Asp Lys Gly Tyr Thr Ser Lys Glu Gln Lys Asp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION

<400> SEQUENCE: 4

Ala Leu Tyr Asp Lys Gly Tyr Thr Ser Lys Glu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthesized Peptide
<220> FEATURE:
<221> NAME/KEY: MISC_FEATURE
<222> LOCATION: (6)..(6)
<223> OTHER INFORMATION: Xaa can be a naturally occurring amino acid,
      absent, a derivatized amino acid, a non-amino acid prosthetic
      group and combinations thereof

<400> SEQUENCE: 5

Asp Cys Val Gly Ile Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: Synthesized Peptide

<400> SEQUENCE: 6

Lys Glu Gln Lys Asp Cys Val Gly Ile Trp
1               5                   10

<210> SEQ ID NO 7
<211> LENGTH: 11
<212> TYPE: PRT
<213> ORGANISM: Artificial Sequence

```
<220> FEATURE:
<223> OTHER INFORMATION: Synthesized Peptide

<400> SEQUENCE: 7

Thr Ser Lys Glu Gln Lys Asp Cys Val Gly Ile
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION

<400> SEQUENCE: 8

Ala Leu Tyr Asp Lys Gly Tyr Thr Ser Lys Glu Gln Lys Asp Cys Val
1               5                   10                  15

Gly Ile

<210> SEQ ID NO 9
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 9

Thr Ser Lys Glu Gln Lys Asp Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 10

Gly Tyr Thr Ser Lys Glu Gln Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION

<400> SEQUENCE: 11

Ala Leu Tyr Asp Lys Gly Tyr Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 12
```

```
Thr Ser Lys Glu Gln Lys Asp
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 13

Lys Glu Gln Lys Asp Cys Val
1               5

<210> SEQ ID NO 14
<211> LENGTH: 7
<212> TYPE: PRT
<213> ORGANISM: Artificial Sequence
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION

<400> SEQUENCE: 14

Ala Leu Tyr Asp Lys Gly Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 15

Ser Lys Glu Gln Lys Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 16

Lys Asp Cys Val Gly Ile
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 17

Lys Glu Gln Lys Asp
1               5

<210> SEQ ID NO 18
<211> LENGTH: 5
<212> TYPE: PRT
<213> ORGANISM: Artificial Sequence
<220> FEATURE:
```

```
<223> OTHER INFORMATION: Synthetic Peptide

<400> SEQUENCE: 18

Gln Lys Asp Cys Val
1               5
```